United States Patent
Johansson et al.

(10) Patent No.: US 9,226,848 B2
(45) Date of Patent: Jan. 5, 2016

(54) PERCUTANEOUS IMPLANT AND OSTOMY METHOD

(75) Inventors: Martin Johansson, Valida (SE); Björn Edwin, Satre (NO); Leif Hulten, Stora Höga (SE); Peter Thomsen, Västra Frölunda (SE)

(73) Assignee: Ostomycure AS, Oslo (NO)

( * ) Notice: Subject to any disclaimer, the term of this patent is extended or adjusted under 35 U.S.C. 154(b) by 1065 days.

(21) Appl. No.: 13/266,876

(22) PCT Filed: Apr. 28, 2010

(86) PCT No.: PCT/GB2010/000851
§ 371 (c)(1), (2), (4) Date: Feb. 3, 2012

(87) PCT Pub. No.: WO2010/125346
PCT Pub. Date: Nov. 4, 2010

(65) Prior Publication Data
US 2012/0123361 A1     May 17, 2012

Related U.S. Application Data

(60) Provisional application No. 61/173,494, filed on Apr. 28, 2009.

(51) Int. Cl.
*A61F 5/44* (2006.01)
*A61F 5/445* (2006.01)

(52) U.S. Cl.
CPC ........... *A61F 5/445* (2013.01); *Y10T 29/49826* (2015.01)

(58) Field of Classification Search
CPC ........... A61F 5/44; A61L 27/00; A61L 27/56; A61B 17/00
See application file for complete search history.

(56) References Cited

U.S. PATENT DOCUMENTS

| | | | |
|---|---|---|---|
| 4,183,357 A | 1/1980 | Bentley et al. | 128/283 |
| 4,217,664 A * | 8/1980 | Faso | 606/108 |
| 5,139,497 A * | 8/1992 | Tilghman et al. | 606/285 |

(Continued)

FOREIGN PATENT DOCUMENTS

| | | |
|---|---|---|
| CN | 101389293 A | 3/2009 |
| EP | 1 632 201 A1 | 3/2006 |
| WO | WO 2007/099500 A1 | 7/2007 |
| WO | WO 2009/024568 A1 | 2/2009 |

OTHER PUBLICATIONS

International Search Report and Written Opinion, PCT/GB2010/000851, mailed Jul. 29, 2010.

(Continued)

*Primary Examiner* — Melanie Hand
(74) *Attorney, Agent, or Firm* — Winston & Strawn LLP (57) ABSTRACT

A percutaneous ostomy implant for implantation into the abdominal wall of a patient. The implant has a cylindrical part for mounting an external detachable device thereto, an ingrowth mesh and a circular flange for anchoring the implant. The cylindrical part and circular flange are attached to opposite ends of the ingrowth mesh. The ingrowth mesh is arranged such that when the implant is implanted in the abdominal wall of a patient, the epidermis meets the ingrowth mesh and is able to attach therethrough directly to serosal tissue of a bowel segment inside the implant.

28 Claims, 6 Drawing Sheets

(56) References Cited

U.S. PATENT DOCUMENTS

2006/0147492 A1* 7/2006 Hunter et al. .................. 424/426
2009/0192464 A1 7/2009 Axelsson et al. ......... 604/164.04

OTHER PUBLICATIONS

Jonsson, Olof et al., "Long-Time Experience with the Kock Ileal Reservoir for Continent Urinary Diversion", Reconstructive Urology, Eur. Urol., vol. 40, pp. 632-640 2001.

Jonsson, Olof et al., "Stabilization of the Nipple Base with Titanium Rings when Reoperating Patients with Continent Urostomiés for Nipple Dysfunction", Scand. J. Urol. Nephro. vol. 30, pp. 51-56 (1996).

Wasmuth H. H., et al. "Surgical load and long-term outcome for patients with Kock continent ileostomy", Colorectal Dis. vol. No. 8, pp. 713-717 . (2007).

* cited by examiner

PERCUTANEOUS IMPLANT AND OSTOMY METHOD

This application is a 371 filing of International Patent Application PCT/GB2010/000851 filed Apr. 28, 2010 which claims the benefit of 61/173,494 filed Apr. 28, 2009.

BACKGROUND

The present invention relates to a percutaneous ostomy implant and a surgical method, which may use that implant, for creating a continent reservoir in communication with a percutaneous port.

Ileostomy and colostomy are common operations which may be necessitated, for example, by malignancy or chronic bowel inflammation. The surgery is called an ileostomy if the colon and rectum are removed and a colostomy if the rectum alone is removed. In these operations, a stoma is formed in the abdominal wall to which the ileum or colon respectively is connected. The stoma in most cases has to be connected to a bag.

However, instead of a conventional ileostomy, it is possible to make a reservoir known as a "Kock pouch" from the distal part of the ileum. It is formed in such a way that nipple valve is created which serves to close the reservoir, whilst allowing it to be drained intermittently by means of a catheter.

Figure 1:
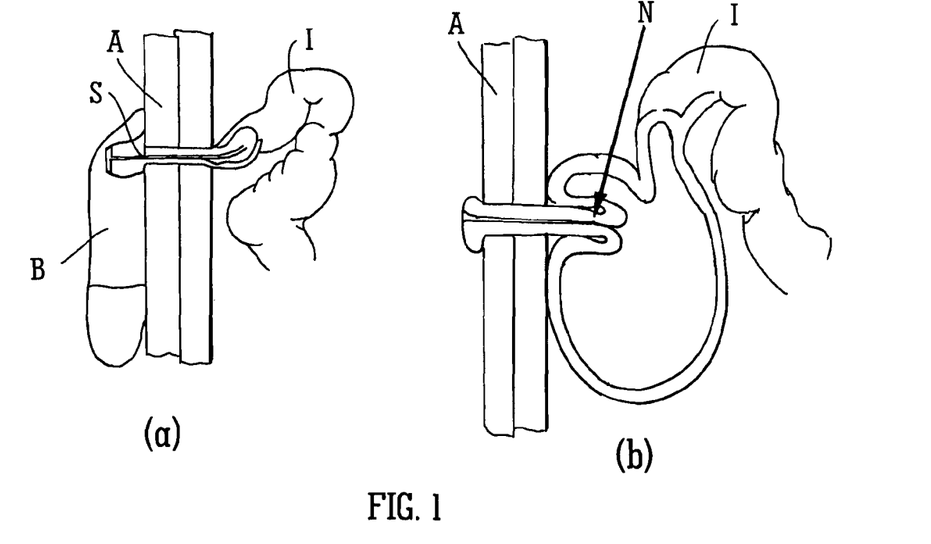
FIG. 1 is a drawing of a conventional ileostomy (a) and a Kock pouch (b)

This is an example of a so-called continent ileostomy (CI); it was formerly an attractive alternative to conventional ileostomy, but is now rarely used. The complexity of the procedure and the high potential for complications—most of them related to dysfunction of the continence nipple valve—has deterred many surgeons from adopting the operation today. FIG. 1 illustrates (a) a conventional ileostomy and (b) a Kock's pouch ileostomy.

The advantages and drawbacks of the Kock pouch are discussed in Wasmuth, H. H., M. Svinsas, et al. (2007). "Surgical load and long-term outcome for patients with Kock continent ileostomy." Colorectal Dis 9(8): 713-7; Olof Jonsson, Gunnar Olofsson, Elisabet Lindholm, Harriet Törnqvist, "Long-Time Experience with the Kock Ileal Reservoir for Continent Urinary Diversion", Reconstructive Urology, Eur Urol 2001; 40:632-640; and Olof Jonsson, Bo Rangert, Frank Aldenborg, Magnus Campanello, Gunnar Wikholm and Staffan Akerlund, "Stabilization of the Nipple Base with Titanium Rings when Reoperating Patients with Continent Urostomies for Nipple Dysfunction", Scand J Urol Nephro 30: 51-56, 1996.

The ileopouch anal anastomosis (IPAA) is today the gold standard worldwide for these patients, but as with a CI, this operation is also risky and failures are common, mostly leading to pouch excision with loss of bowel. Conversion of a failed IPAA to a CI would be a preferable option but again, surgeons are again reluctant to perform this complex and unreliable technique.

In their earlier patent application EP 1632201-A1, the present applicants disclosed a percutaneous ostomy implant comprising a solid-walled cylindrical body and an anchoring section in the form of a circular flange. The device was designed to be implanted through the abdominal wall and secured by the anchoring section which was located below the muscle layer. This section comprised inner and outer concentric rings interconnected by S-shaped members in order to provide an axially resilient structure which could absorb shear stresses and consequently reduce the risk of tissue damage. Spaces around the S-shaped members and provision of numerous apertures in the rings allowed for tissue ingrowth and vascularisation. It was proposed to connect the device to the side of the vessel (colon etc.) wall and by providing a removable lid a continent ostomy could be provided.

A development of this implant was disclosed in WO 2007/099500 in which the single solid-walled cylindrical body of EP 1632201-A1 was replaced by an outer skin-penetrating ring-like part spaced from the anchoring section by circumferentially-spaced legs. This implant was designed to receive a vessel drawn up through it; the spaces between the legs allowed the generation of a tissue bond between the inner part of the abdominal wall and the serosal tissue of the bowel in order to provide a more secure, stable, leak-proof and well-vascularised skin-implant junction. In some embodiments, a circumferential ingrowth mesh was additionally provided. This extended along most of the length of the cylindrical body with an annular gap being provided between it and the outer ring-like part to allow tissue to grow through the mesh within the outer ring-like part.

In a further development, in WO 2009/024568, the present applicants proposed a cylindrical body formed of two axially-spaced tubular parts. The outer tubular part penetrated the skin and was provided with means for connection to a bag or lid. The inner tubular part was attached to an anchoring flange of the type previously described. The two parts were connected together by a "distance means" comprising either radially-spaced legs or a rigid cylindrical ingrowth mesh which allowed for the generation of a tissue bond between the abdominal wall and the bowel. By means of this arrangement, a break was provided in the possible infection path along the implant from the skin. Furthermore, the outer tubular part penetrated the skin surface thereby isolating the skin surface—where sources of infection may be present—from the bowel tissue.

SUMMARY OF THE INVENTION

According to a first aspect of the present invention, there is provided a percutaneous ostomy implant for implantation into the abdominal wall of a patient, the implant comprising: a cylindrical part for mounting an external detachable device thereto; a preferably cylindrical ingrowth mesh; and a circular flange for anchoring the implant; the cylindrical part and circular flange being attached to opposite ends of the ingrowth mesh; wherein the ingrowth mesh is arranged such that when the implant is implanted in the abdominal wall of a patient, the epidermis meets the ingrowth mesh and is able to attach therethrough directly to serosal tissue of a bowel segment inside the implant.

Thus, the present invention is based on the hypothesis that by allowing the epidermis to attach directly to the serosal tissue, bacterial infection (i.e. bacterial attachment to implant surface and subsequent migration) can be prevented. This is in marked contrast to the previously-described implant configurations which have prevented this attachment by means of a solid-walled skin-penetrating parts, which were arranged to isolate the epidermis from the serosal tissue. Provided that the attachment of the serosal tissue above the epidermis-serosal junction to the mesh structure is stable and does not retract down to the level of the junction, a stable system can be achieved.

Thus, the implant of the present invention may be formed with the cylindrical part in the form of a ring or squat cylinder, which is configured to be entirely exposed outside the abdominal wall. Typically, the exterior surface of the mesh is exposed and unobstructed to allow direct and unbroken contact with the abdominal wall in the region adjacent to the circular flange as well as adjacent to the epidermis; this permits tissue ingrowth through the mesh from its connection to the circular anchoring flange to the skin surface.

It will be appreciated that the axial extent of the ingrowth mesh below (i.e. axially towards the centre of the patient) the cylindrical part must be sufficient for the cylindrical part to remain above the surface of the patient's skin. Thus, the ingrowth mesh comprises a skin-penetrating portion having an axial length that is greater than the thickness of the tissue layers above the muscle layer. Typically, it will be greater than the axial extent of the cylindrical part.

As is known from the applicant's prior patent applications, the circular flange is preferably penetrated by multiple small holes to allow ingrowth of connective tissue. The circular flange preferably comprises inner and outer concentric rings, the inner ring being attached to one end of the cylindrical mesh and the outer ring being connected to the inner ring by a plurality of S-shaped connecting members.

The ingrowth mesh may be a laser-cut titanium ingrowth structure and it may be laser-welded to the cylindrical part and circular flange.

Preferably the cylindrical part is radially outwardly spaced from the mesh, which extends inside it, in the manner known from WO 2007/099500, so that an annular gap is provided. As in the prior art implant, in the preferred form of the present invention the annular gap allows for the ingrowth of serosal tissue from the vessel. This forms the above-mentioned attachment above the epidermis-serosa junction. However, in contrast to the prior art, this tissue will be contiguous with, not isolated from, the epidermis surrounding the implant.

The provision of an epidermis-serosa attachment surface is believed to be a further inventive concept in itself and therefore, viewed from a further aspect, the invention provides a percutaneous ostomy implant comprising a preferably cylindrical ingrowth mesh structure configured in use to surround a vessel (e.g. a bowel segment) having serosal tissue and to allow epidermis to attach directly to the serosal tissue through the ingrowth mesh. Preferably the mesh extends above (i.e. outwardly of) the epidermis-serosa junction, so that serosal tissue may attach to the mesh so as to form a stable structure in which the attachment will not retract down to the level of the epidermis-serosa junction.

Although the implant may be made of any biologically-acceptable material, e.g. plastics, it is preferably formed of commercially pure titanium, preferably ASTM Grade 2 titanium, which may have a surface treatment, such as a grit or an aluminium oxide-blasted surface and/or an electrochemical treatment to achieve optimum topographical properties, physical and chemical surface characteristics (e.g. surface roughness) etc.

The implant is preferably used in combination with an external detachable device mounted to the cylindrical part of the implant. In the context of a continent system, this is preferably a lid. However, the implant could be used with a bag. Furthermore, as will be discussed more fully below, the implant may be used in conjunction with a so-called healing device which stabilises the implant and prevents relative movement between the tissue and implant as it heals.

In summary, the most preferred form of the implant of the present invention is made of commercially pure titanium (grade 2) machined to the desired shape and blasted with aluminium oxide. It consists of a cylindrical part and a circular flange. The circular flange is penetrated with multiple small holes to allow ingrowth of connective tissue. The two parts are connected to a cylindrical mesh. The cylindrical mesh is a laser-cut titanium ingrowth structure attached to the cylinder and flange by means of laser welding.

The implant is preferably decontaminated with ultrasonic cleaning in detergent and alcohol followed by sterilisation by means of autoclaving.

It will be appreciated that the invention extends to a method of making an implant comprising providing the components set out above (preferably the preferred forms of the components set out above) and assembling them, preferably by means of laser welding.

The method preferably includes the step of dimensioning the skin-penetrating portion of the ingrowth mesh such that it has an axial length that is greater than the thickness of the tissue layers above the muscle layer for a given patient or class of patients into which it may be implanted.

Thus, viewed from a further aspect there is provided a method of manufacturing a percutaneous ostomy implant for a patient or class of patients comprising the steps of providing: a cylindrical part for mounting an external detachable device thereto; a preferably cylindrical ingrowth mesh; and a circular flange for anchoring the implant; attaching the cylindrical part and circular flange to opposite ends of the ingrowth mesh; wherein the ingrowth mesh is dimensioned such that if the implant is implanted immediately above the muscle layer in the abdominal wall of the patient or a member of the class of patients respectively, the epidermis would meet the ingrowth mesh and be able to attach therethrough directly to serosal tissue of a bowel segment inside the implant.

Viewed from another aspect, the invention provides a method of implanting an ostomy implant into the abdominal wall of a patient, the method comprising: providing implant having: a cylindrical part for mounting an external detachable device thereto; a preferably cylindrical ingrowth mesh; and a circular flange for anchoring the implant; the cylindrical part and circular flange being attached to opposite ends of the ingrowth mesh; and implanting the implant into the abdominal wall of a patient such that the epidermis meets the ingrowth mesh and is able to attach therethrough directly to serosal tissue of a bowel segment inside the implant.

It will be appreciated that the method typically will further comprise drawing a bowel segment through the implant such that the serosal tissue of the bowel contacts the epidermis through the ingrowth mesh, whereby an ostomy is formed.

The method may include the step of selecting an implant for the patient such that the ingrowth mesh has a skin-penetrating portion having an axial length that is greater than the thickness of the tissue layers above the muscle layer.

As discussed above, the preferred forms of the implant allow attachment of serosal tissue to an axially extending cylindrical mesh surface within the cylindrical part.

Viewed from a further aspect, the invention provides a method of performing an ostomy comprising providing a cylindrical ingrowth mesh structure, surrounding a vessel (e.g. a bowel segment) having serosal tissue with said mesh structure (e.g. by drawing the vessel therethrough) and allowing epidermis to attach directly to the serosal tissue through the ingrowth mesh. Preferably the mesh structure is arranged such that attachment of serosal tissue to the mesh structure extends above (i.e. outwardly of) the epidermis-serosa junction, so as to form a stable structure in which the attachment will not retract down to the level of the epidermis-serosa junction.

The applicants have found that the implant of the invention allows a continent ostomy to be provided because the natural resilience of the vessel tissue (which is constricted to some extent where it is drawn into the implant) occludes the aperture through the implant and results in a valve being formed. Provided that a reservoir is formed so that fluid pressure is restricted, the valve enables the ostomy to be continent. It may be drained using a catheter in the known manner. A lid is preferably provided to provide further protection against leakage and to protect the exposed vessel.

Thus, viewed from a further aspect the invention provides a method of performing a continent ostomy comprising: implanting a percutaneous ostomy implant in the abdomen; drawing a section of vessel (e.g. bowel) into the implant; and securing it to form a stoma; wherein the internal diameter of the implant is selected to constrict the vessel such that the natural resilience of the vessel tissue resiliently occludes the stoma, thereby forming a valve.

The implant and/or method are preferably as set out herein.

This aspect of the invention also extends to an ostomy implant dimensioned to form a continent ostomy by means of the above method and to a method of manufacturing such an implant which comprises the step of dimensioning the implant for a given patient or class of patients such that a valve will be formed when the implant is used in such method. Again, the method of manufacture is preferably as set out herein. The implant is preferably used or provided in combination with a lid to prevent leakage and/or to protect the stoma.

As noted above, a healing device may be used after surgery and so the method preferably further comprises mounting a healing device to the cylindrical part of the implant during the healing phase in order to protect the implant and/or prevent it from being retracted below skin level. Once healing is complete, as discussed above, a lid may be mounted to the cylindrical part of the implant.

The method preferably uses an implant having the preferred features described above.

As set out above, the use of a healing device is an important feature of certain aspects of this invention. Thus, viewed from another aspect, the invention provides a method for providing a percutaneous port for continent ostomy in a subject in need of the same, which comprises percutaneous implanting of an ostomy implant in the abdominal wall of the subject for encircling and engaging an externalised length of a body duct, and providing a healing device to prevent the implant from being distracted below the abdominal wall of the subject.

Preferably, the implant comprises a body that includes an exterior ring section at least a part of which protrudes outwardly from the abdominal wall with a free end, and an interior section extending through the abdominal wall and inside the patient for internal fixation of the implant, with the exterior ring section and interior section having a common axis. Thus, the implant may be as set out above and preferably has the preferred features set out above.

The healing device may serve to sealingly close the protruding part and free end of the implant body to promote healing.

The method preferably further comprises creating a pocket between external fascia and subcutis of the subject; creating a channel through the rectus muscle and the peritoneum of the subject; if necessary, securing and stabilising the implant to the overlaying fascia and the underlying muscle; creating a channel through the subcutis and skin; inserting the cylindrical part of the implant through the skin; closing the pocket; pulling the terminal ileum of the reservoir through the abdominal wall and the implant; and attaching the healing device to the implant.

The method of this aspect of the invention preferably uses an implant comprising a body section having an exterior ring section, at least a part of which protrudes outwardly from the abdominal wall with a free end, and an interior section extending through the abdominal wall and inside the patient for internal fixation of the implant, with the exterior ring section and interior section having a common axis; the healing device is preferably engaged with the implant body to prevent the implant from being distracted below the abdominal wall of the subject, the healing device also preferably serving for sealingly closing the protruding part and free end of the implant body.

As disclosed herein, the specific structure of the implant body can vary and (as well as those structures set out above) can, for example, include any one of the structures disclosed in WO2007/099500A1, WO2009/024568A1 or EP 1632201 A1. The body preferably also includes mating means for removable attachment to the healing device.

The healing device preferably further includes cap or lid that surrounds and sealingly closes the protruding part of the implant, and preferably also mating means for removable attachment to the mating means of the implant body.

In a preferred arrangement, the cap means of the healing device further includes an O-ring serving for sealing against the exterior circumferential wall of the implant, and the implant body includes a healing plate which in use rests on the skin surface of the subject, with the healing plate having an external screw thread for coupling with a complementary internal screw thread on the cap means.

It will be seen that various aspects of the present invention, at least in their preferred forms:

(a) provide healing and tissue ingrowth into the different structures of an implant used for providing an ostomy, (b) construct a continent urostomy, ileostomy or other kind of ostomy, (c) minimize the risk of bacterial infection when making ostomies, and (d) provide a new technique using a percutaneous implant to replace the problematic continence nipple valve of the CI.

BRIEF DESCRIPTION OF THE DRAWINGS

Embodiments of the invention will now be described, by way of example only, and with reference to the accompanying drawings.

DETAILED DESCRIPTION OF THE INVENTION

With reference first to FIG. 1(a), there is illustrated a conventional ostomy where a stoma S is formed in the abdominal wall A through which the intestine I may be connected to a bag B. FIG. 1(b) illustrates the alternative Kock pouch surgical technique in which a nipple valve N is formed from a part of the intestine I in order to create a continent ostomy.

Figure 2:
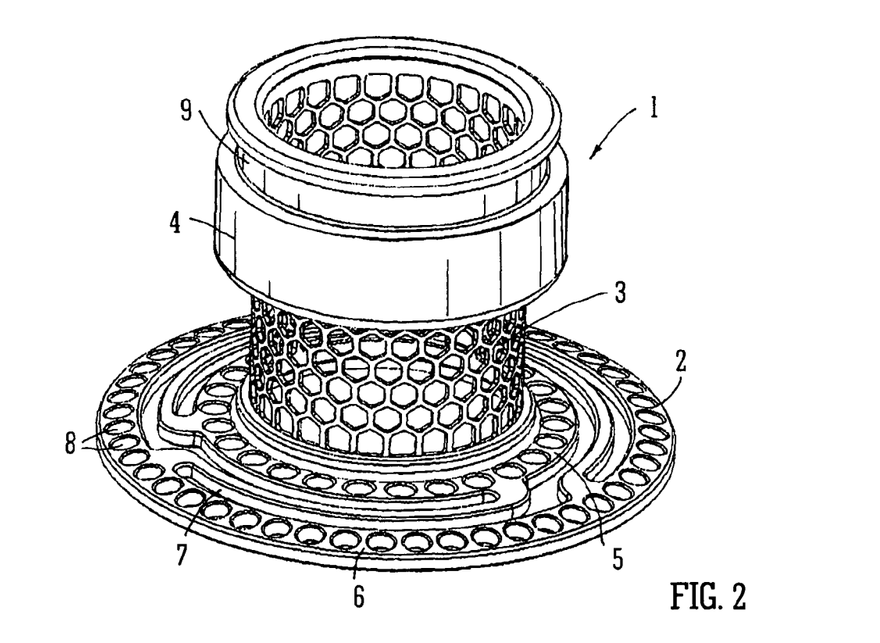
FIG. 2 is a perspective view of an implant according to an embodiment of the invention.
Figure 3:
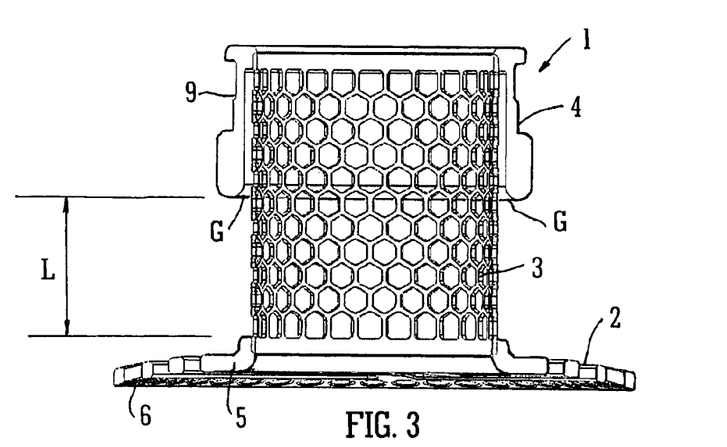
FIG. 3 is a cross-sectional view of the implant of FIG. 1.

FIGS. 2 and 3 illustrate an embodiment 1 of an implant according to an embodiment of the invention. It comprises a circular anchoring flange 2, a cylindrical mesh cylinder 3 and a cylindrical end part 4. The implant is formed from machined titanium, with the various components laser-welded together.

It will be noted that an annular gap G (FIG. 3) is formed between the inner face of the cylindrical end part 4 and the outer face of the mesh cylinder 3.

The anchoring flange 2 is as described in the applicant's earlier patent applications referred to in the introduction. It has inner 5 and outer 6 concentric rings connected by S-shaped members 7 to form an axially resilient structure. A multitude of holes 8 are provided to allow ingrowth of tissue through the rings.

The mesh cylinder 3 is formed from a machining and laser cutting process.

The end part 4 is in the form of a connection ring. It has a circumferential groove 9 to allow for the connection of detachable devices such as lids, bags and healing devices (see below).

Figure 4:
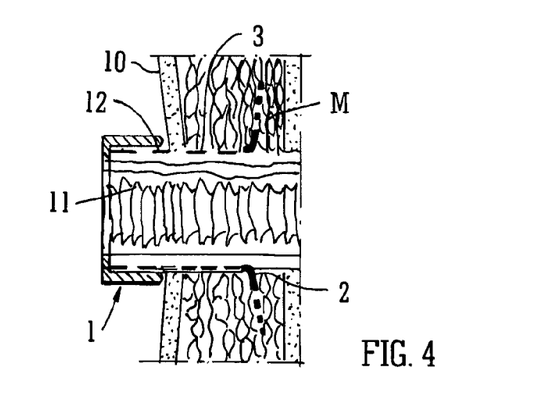
FIG. 4 is a cross-sectional view of the implant of FIG. 1 implanted in the abdominal wall of a patient.
Figure 5:
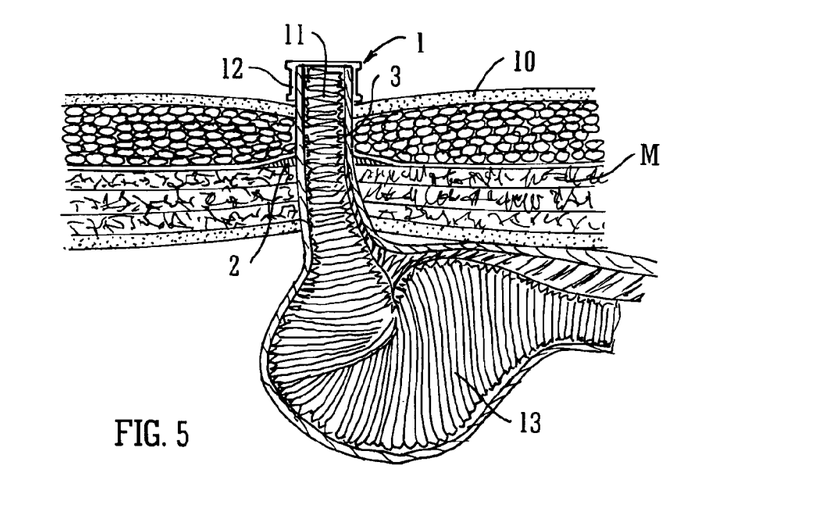
FIG. 5 is a view corresponding to that of FIG. 4, showing a pouch to which the implant is connected.

FIGS. 4 and 5 illustrate the implant 1 in use after it has been implanted in a patient. It will be noted that the circular anchoring flange 2 is located immediately above the muscle layer M and that the length L of the skin-penetrating part of the mesh cylinder 3 is sufficient that the end part 4 is entirely clear of the surface of the epidermis 10 of the abdominal wall. Thus, unlike the outer bag or lid-connecting parts of the prior art implants discussed above, it does not penetrate the skin. As discussed below, different lengths of implant may be provided as necessary. The implant may, for example, have any of the dimensions set out in Tables 1 and 2 below.

A section of bowel 11 is externalised through the internal diameter of the mesh cylinder 3. As noted above, the epidermis 10 meets the ingrowth mesh 3, and is therefore able to contact the serosal surface 12 of the bowel 11. As healing takes place, the tissues grow through the mesh cylinder 3 to provide attachment between abdominal wall tissue, including the epidermis and bowel. Furthermore, as shown most clearly in FIG. 4, the serosal tissue is able to grow into the annular gap G. In addition to this, tissue ingrowth occurs through the anchoring flange 2 and through other parts of the ingrowth mesh, in the known manner.

FIG. 5 illustrates the relationship between the implant 1 and a pouch 13 formed in the bowel in the known manner. Because the resilient tissue that forms the bowel is constricted as it passes through the implant to form a valve, this provides a continent system such that the pouch may be emptied at intervals using a catheter in a similar manner to the Kock pouch. A removable lid (not shown) may additionally be provided to prevent leakage and to protect the stoma. Thus, there is no need for a bag.

The remaining figures illustrate the method of an embodiment of the invention in which a healing device is employed. The implant may be that of the embodiment described above, or another type e.g. be the implant according to the applicants own International patent applications WO 2007/099500 A1, WO 2009/024568 A1 or EP1632201 A1, the contents of each of which are expressly incorporated herein by reference thereto. Thus, the implant is e.g. made of commercially pure titanium Gr. 2, machined to desired shape, and blasted with aluminium oxide. Other biological acceptable materials, e.g., plastics, can also be used. The preferred materials are dimensionally stable materials that can resist sterilization and use in medial treatments.

Figure 8:
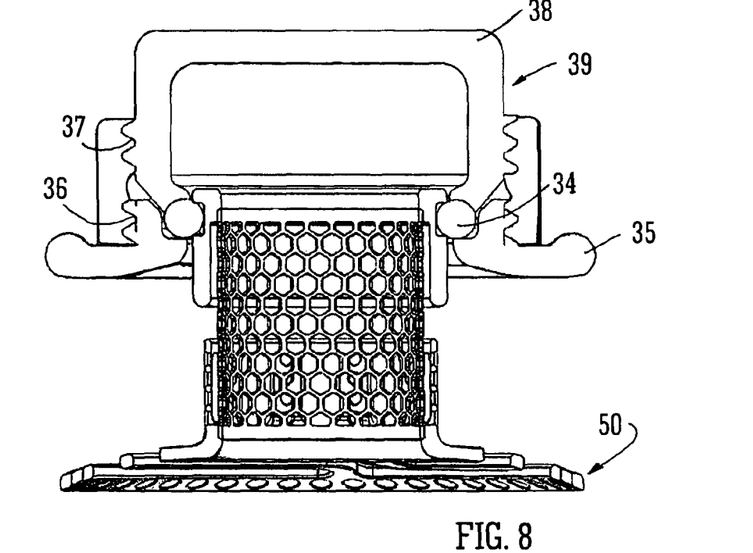
FIG. 8 is a partially-sectioned elevation of a healing device attached to the free protruding end of a known implant.
Figure 9:
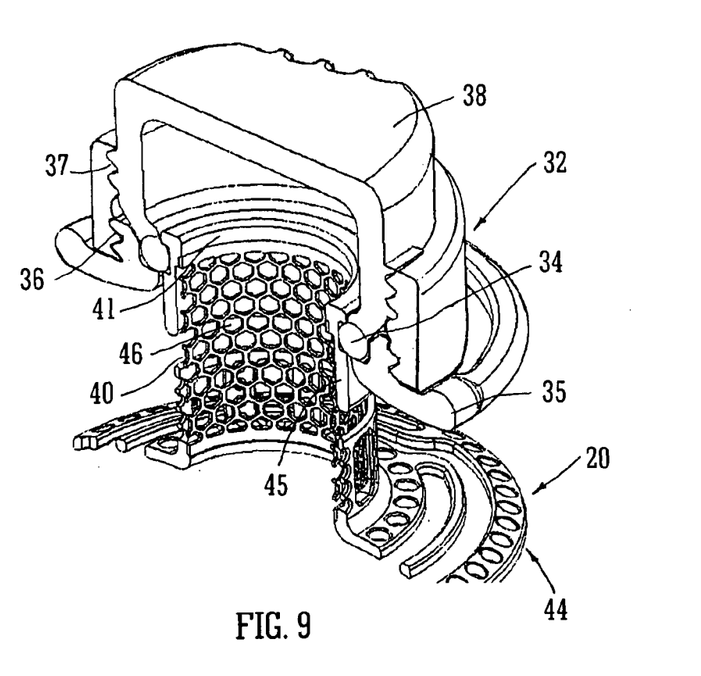
FIG. 9 is a sectioned perspective view corresponding to FIG. 8.
Figure 10:
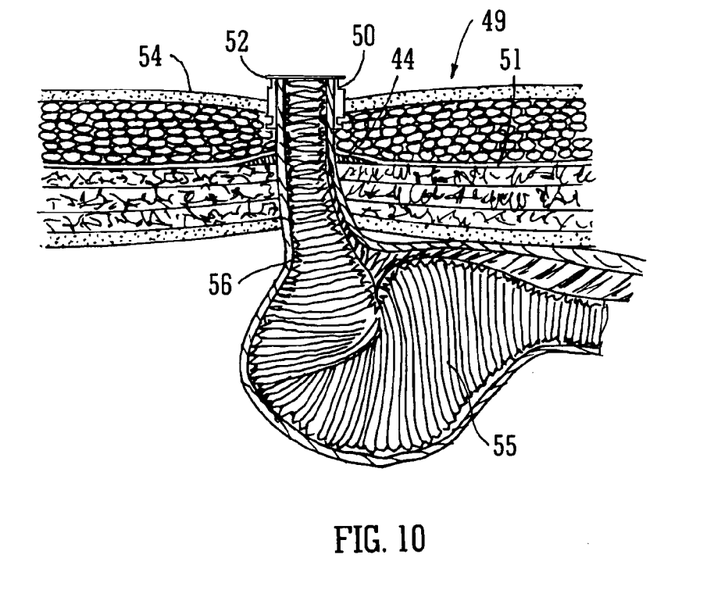
FIG. 10 shows the (known) implant of FIGS. 8 and 9 implanted in a patient prior to the addition of the healing device.

The implant 20 of this embodiment consists of a cylinder 21 ending with a circular flange 22. The cylindrical portion closest to the flange is formed by ribs 24 allowing ingrowth of connective tissue to prevent epithelial downgrowth and promote connective tissue interdigitation. The ribs 24 have numerous holes 25. The rest of the cylindrical portion is solid-walled. The previously-mentioned applications can be referred to for further details of this implant. The circular flange 22 is penetrated with multiple small holes 23 to allow ingrowth of connective tissue. A laser cut titanium ingrowth mesh 26 is integrated by means of laser welding on the inside of the cylinder.

The first stage of the method is for the implant and the instrumentation to be decontaminated with ultrasonic cleaning in detergent and alcohol followed by sterilization by means of autoclaving.

Several sizes of the implants are available with various height and inner diameters. The version to be used is chosen intra-operatively and is mostly dependent on the anatomy. Examples of dimensions used in animal experiments are given in Table 1 below.

TABLE 1

Examples of implant configurations (canine).

| Designation | Inner diameter | Height |
|---|---|---|
| P15 Small | 15 mm | 21.7 mm |
| P15 Medium | 15 mm | 24.2 mm |
| P15 Large | 15 mm | 28.8 mm |
| P15 Small 17.5 | 17.5 mm | 21.7 mm |

For human use, larger sizes are required, as set out in Table 2:—

TABLE 2

Examples of implant configurations (human).

| Designation | Inner diameter | Height |
|---|---|---|
| P16 Small | 22 mm | 25 mm |
| P16 Medium | 22 mm | 35 mm |
| P16 Large | 24 mm | 25 mm |
| P16 Large 35 | 24 mm | 35 mm |

Figure 6:
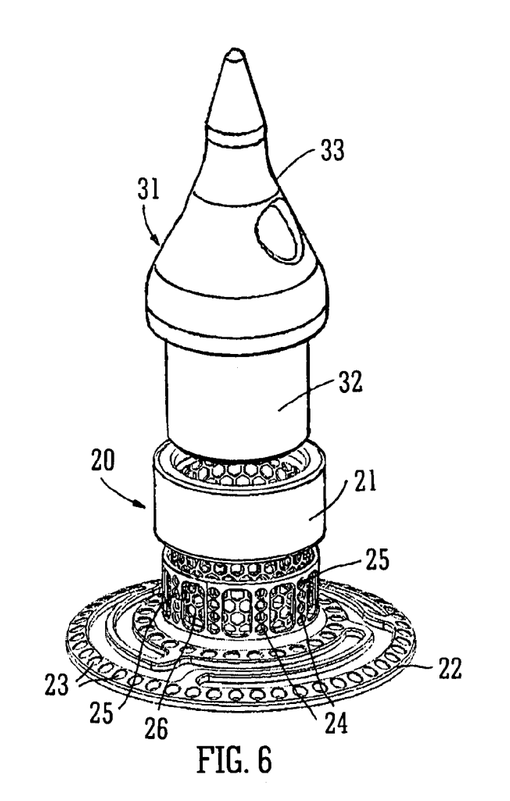
FIGS. 6 and 7 are perspective views of a specially designed insertion instrument for positioning an implant in the abdominal wall.
Figure 7:
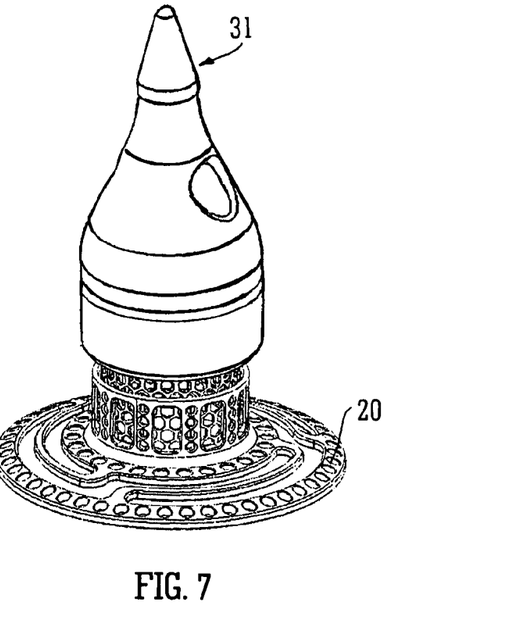

As shown in FIGS. 6 and 7, a specially designed insertion instrument, an insertion cone 31, is used for facilitated positioning of the implant 20 in the abdominal wall. The insertion cone 31 has a lower cylindrical part 32 that fits snugly inside the implant and a generally conical upper part 33 which is designed to be pushed through a resilient opening in the abdominal wall. Thus, the cone 31 is fitted to the implant 20 and then they are pushed through the skin. For the creation of a circular cut through epidermis a (e.g. 8 mm) biopsy skin punch is preferably used (e.g., Steifel, Germany), though a scalpel may be used.

As shown in FIGS. 8 and 9, a healing device 39 is provided for attachment to the free protruding circular end of the implant 20 during the healing phase. The healing device 39 protects the implant and prevents the implant from being retracted below the skin level. The healing device 39 comprises a healing plate 35 which is designed to rest on the skin surface. The healing plate is provided with an external screw thread 36 for coupling with a complementary internal screw thread 37 of an optional cap 38 which can be used to surround and sealingly close the protruding part of the implant 20 at least during healing, and optionally also subsequently. It may also include an O-ring 34 serving for sealing against the exterior circumferential wall of the implant 20.

The healing device is shown attached to a further design of implant 50. The interior section of it comprises an intermediate section 40 emerging from the exterior ring 41 that is axially divided into a first intermediate section part and a second intermediate section part emerging from the first intermediate section part, with the interior section extending into an anchoring section 44. The second intermediate section part or intermediate section comprises circumferentially spaced apart first connection members 45 connecting the second intermediate section part or the intermediate section with the anchoring section 44. Integrated ingrowth mesh 46 is provided along the internal circumference of the second intermediate section part or the intermediate section.

EXAMPLE OF EXPERIMENTAL PROCEDURE

Female Labrador dogs, weighing approximately 25 kg at implantation, are used as experimental animals. The animals are prepared, anaesthetized and monitored according to the local ethics committee application.

One device is implanted in each animal. The experiment is a two-stage procedure. In the first procedure, the device is implanted and an isolated ileal reservoir is constructed and connected to the implant. In the second procedure, one ureter is connected to the reservoir creating a urostomy.

Operative Procedure—Stage One

The implant 50 is placed in the abdominal wall 49 as illustrated in FIG. 10. (Note that this implant is not implanted in the same manner as implant 1 discussed above.) The subcutaneous flange 44 is placed on the external fascia 51 and the cylindrical portion 52 protrudes through the skin 54. An ileal reservoir 55 is constructed and the terminal ileum 56 of the reservoir is pulled through the abdominal wall 49 and the implant 50. The ileal reservoir 55 is kept isolated from the bowel. The implant 50 and reservoir 55 are left to heal for three weeks with the implant positioned above the muscle and the ileal reservoir attached to the implant.

Surgical stage one may include the following steps for construction of the isolated ileum reservoir 55 and application of implant 50:
1. Placing the animal in a dorsal recumbency.
2. Preferably thoroughly shaving the area around the implant site.
3. Making a suitable abdominal incision, e.g., a midline 10-12 cm abdominal incision.
4. Examining the small intestine and determine where to take an ileum segment.
5. Dividing ileum with stapler, e.g., about 20-30 cm from the ileo-caecal valve.
6. Constructing the reservoir ad modum Kock with e.g., 2×7-15 cm ileal limbs.
7. Restoring the intestinal continuity by a side-to-side anastomosis, e.g., by stapling or suturing.
8. Preferably leak testing the reservoir and measuring the volume.
9. Lateral of the incision making a small circular incision through the skin using e.g., a 8 mm dermis punch instrument or a scalpel.
10. By blunt dissection, creating a pocket between external fascia and subcutis.
11. Creating a channel through the rectus muscle and the peritoneum.
12. Assembling the implant and the insertion cone and driving it through external fascia, subcutis and the skin, via the pocket, and removing the insertion cone.
13. If possible, securing and stabilising the implant by placing nonresorbable sutures in each quadrant of the subcutaneous anchor's outer ring, and connecting these sutures to the overlaying fascia and the underlying muscle.
14. Closing the pocket with e.g., sutures.
15. Pulling out the terminal ileum of the reservoir through the abdominal wall and the implant. The efferent ileum is not everted and sutured to the skin. The efferent segment shall protrude well beyond the implant neck by about 2-3 cm. If needed the efferent ileum is secured with e.g., sutures attached to the healing plate.
16. Flushing the inside of the implant with antibacterial agent, e.g., garamycin.
17. Securing the reservoir to peritoneum with a couple of nonresorbable sutures or similar securing means.
18. Attaching the healing device to the implant.
19. Optionally a catheter is introduced through the implant and secured to the healing plate.
20. Closing the abdominal incision.
Operative Procedure—Stage Two Stage two is performed 3-4 weeks after implantation.

The left ureter was identified and removed from the bladder. The distal end was attached to the reservoir.

A Ch 4 feeding tube (Unomedical, Denmark) is introduced, passing the anastomosis with the free end on the outside. The tube is secured with Vicryl Rapis 4-0 suture in the ureter and to the healing plate outside the abdomen. The tube was flushed with NaCl.

Figure 11:
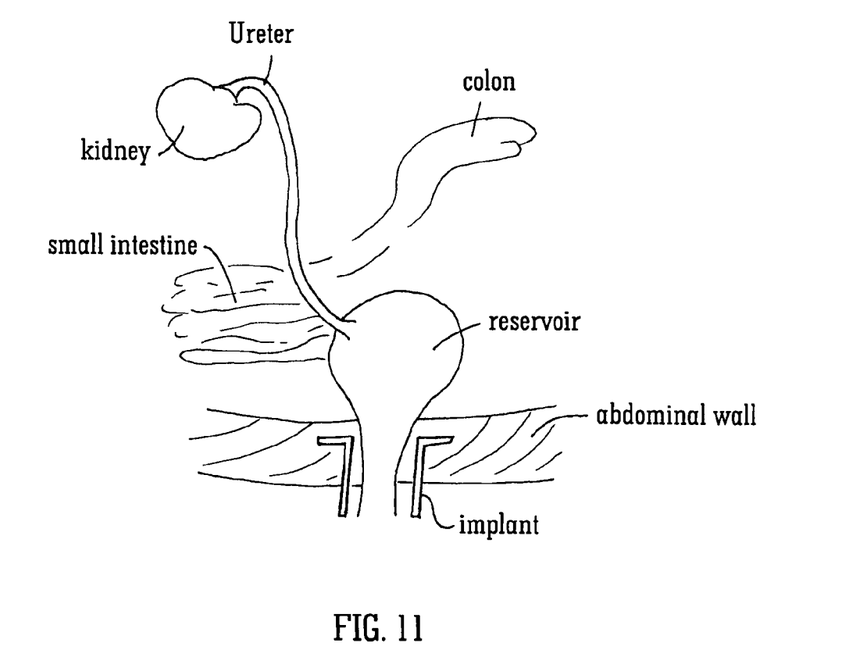
FIGS. 11 and 12 illustrate the completion of the method of an embodiment of the invention where continuity through the implant is restored.
Figure 12:
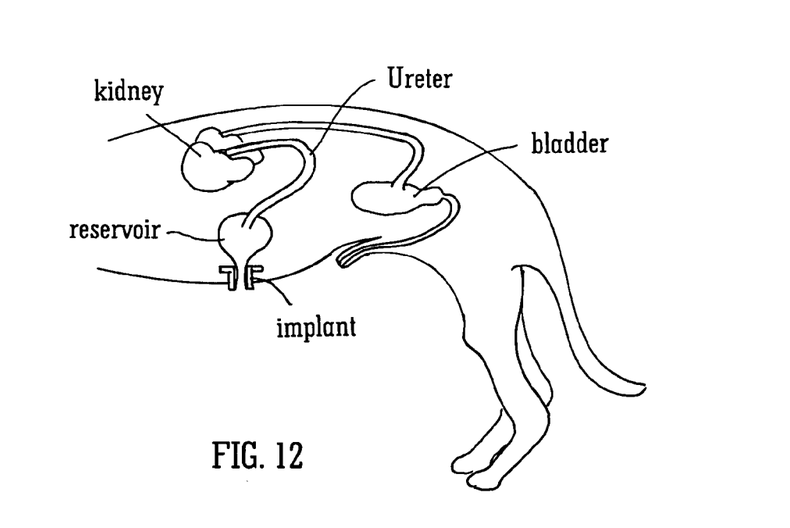

Thus as illustrated in FIGS. 11 and 12, continuity through the implant is restored.

Postoperative Care

Postoperative care and nursing are carried out according to the ethical application and instructions (SOP's).

When the technique is applied to human patients the two stages described above are preferably combined into a single stage.

Figure 13:
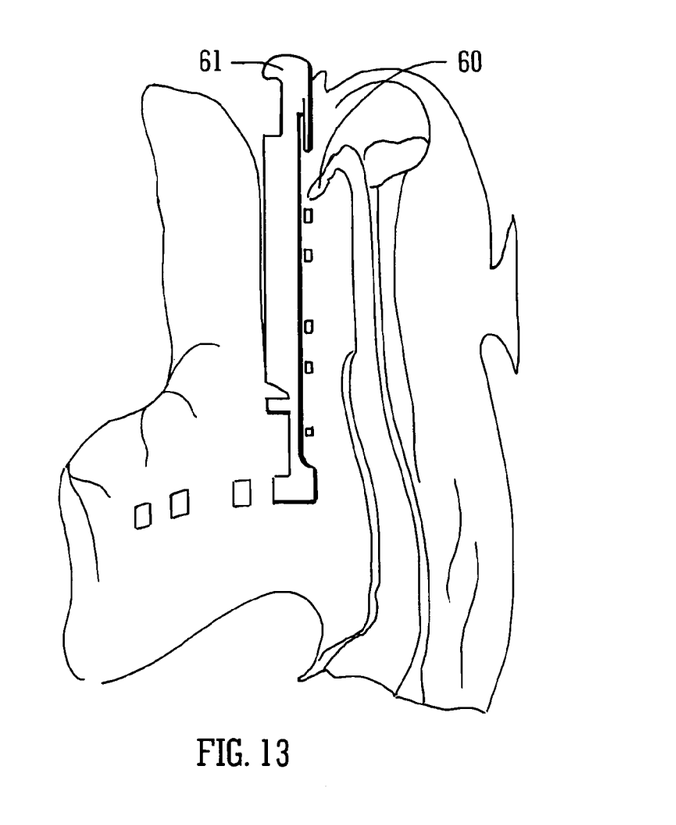
FIG. 13 is a light micrograph of an implanted ostomy implant according to an embodiment of the invention.

FIG. 13 shows a light micrograph demonstrating soft tissue integration and attachment of the serosa of ileum 60 with the titanium implant 61 illustrating that the serosal side of the intestine was adequately attached to this tissue. Histological examination of the ten samples demonstrated that the mesh structure inside the implant was in close contact with regenerated and well-vascularised collagenous tissue, with moderate signs of infection. Thus histology showed soft tissue integration and attachment of the serosa of ileum with titanium.

Experiments have confirmed that, contrary to the previously known surgical procedures, a permanent continent ostomy can be achieved by attaching the efferent bowel segment to a percutaneous titanium implant and that the nipple valve can be dispensed with.

The histological results demonstrate that skin and subcutaneous tissue integrate well with the outer face of the implant and that also the serosal surface of the intestine integrates and merge with the inner face of the implant.

Thus the present technique replaces the problematic nipple valve and offers a reliable continence valve for the Kock pouch and might imply a revival of interest and a renaissance for the procedure in humans. Conversion of a failed IPAA is just another indication for the Kock pouch.

What is claimed is:
1. A percutaneous ostomy implant for implantation into the abdominal wall of a patient, the implant comprising:
a cylindrical part for mounting an external detachable device thereto;

an ingrowth mesh; and a circular flange for anchoring the implant;

wherein the cylindrical part and circular flange are attached to opposite ends of the ingrowth mesh;

wherein the ingrowth mesh has an exterior surface that is exposed and completely unobstructed to allow direct and unbroken contact with the abdominal wall in the region adjacent to the circular flange as well as adjacent to the epidermis, thereby permitting tissue ingrowth through the mesh from its attachment to the flange to the skin surface, and wherein the cylindrical part is spaced sufficiently from the flange axially such that when the implant is implanted in the abdominal wall of a patient, the ingrowth mesh is arranged to meet and contact the epidermis of the patient so that the epidermis can infiltrate the ingrowth mesh and attach therethrough directly to serosal tissue of a bowel segment located inside the implant.

2. The implant according to claim 1, wherein the circular flange is penetrated by multiple small holes to allow ingrowth of connective tissue.

3. The implant according to claim 1, wherein the ingrowth mesh is a laser-cut titanium ingrowth structure.

4. The implant according to claim 1, wherein the ingrowth mesh is attached to the cylindrical part and circular flange by laser-welding.

5. The implant according to claim 1, formed of commercially pure or grade 2 titanium.

6. The implant according to claim 1, having a roughened surface formed by aluminum oxide-blasting.

7. The implant according to claim 1, wherein the circular flange comprises inner and outer concentric rings, the inner ring being attached to one end of the ingrowth mesh and the outer ring being connected to the inner ring by a plurality of S-shaped connecting members.

8. The implant according to claim 1, wherein the exterior surface of the ingrowth mesh is exposed to allow direct and unbroken contact with the abdominal wall in the region adjacent to the circular flange.

9. The implant according to claim 1, wherein the ingrowth mesh is cylindrical.

10. The implant according to claim 9, wherein an annular gap is provided between the inner face of the cylindrical part and the ingrowth mesh.

11. The implant according to claim 1 in combination with an external detachable device mounted to the cylindrical part of the implant.

12. A method of implanting an ostomy implant into the abdominal wall of a patient, which method comprises:

providing an implant according to claim 1; and implanting the implant into the abdominal wall of a patient such that the epidermis meets the ingrowth mesh and is able to attach therethrough directly to serosal tissue of a bowel segment inside the implant.

13. The method according to claim 12, which further comprises drawing a bowel segment through the implant such that the serosal tissue of the bowel contacts the epidermis through the ingrowth mesh.

14. The method according to claim 12, which further comprises mounting a healing device to the cylindrical part of the implant during the healing phase in order to protect the implant and prevent it from being retracted below skin level.

15. The method according to claim 12, which further comprises mounting a lid to the cylindrical part of the implant.

16. In a percutaneous ostomy implant, the improvement comprising an ingrowth mesh structure configured in use to surround a vessel having serosal tissue, a cylindrical part at one end of the mesh structure and a circular flange at the opposite end of the mesh structure for anchoring the implant, wherein the ingrowth mesh has an exterior surface that is exposed and completely unobstructed to allow direct and unbroken contact with the abdominal wall in the region adjacent to the circular flange as well as adjacent to the epidermis, thereby permitting tissue ingrowth through the mesh from its attachment to the flange to the skin surface, and wherein the ingrowth mesh is arranged to be spaced sufficiently axially away from the flange in order to meet and contact the epidermis of the patient and to allow the epidermis of the abdominal wall to infiltrate the ingrowth mesh and attach directly to the serosal tissue in the implant through the ingrowth mesh.

17. The implant according to claim 16, arranged such that the attachment of serosal tissue to the ingrowth mesh may extend above or outwardly of the epidermis-serosa junction.

18. A method of performing an ostomy comprising providing a percutaneous ostomy implant according to claim 16, surrounding a vessel having serosal tissue with the mesh structure and allowing epidermis to attach directly to the serosal tissue through the ingrowth mesh.

19. The method according to claim 18, wherein the mesh structure is arranged such that attachment of serosal tissue to the ingrowth mesh extends above the epidermis-serosa junction, so as to form a stable structure.

20. A method of manufacturing a percutaneous ostomy implant according to claim 16 for a given patient or class of patients which comprises:

providing a cylindrical part for mounting an external detachable device thereto; a cylindrical ingrowth mesh; and a circular flange for anchoring the implant;

attaching the cylindrical part and circular flange to opposite ends of the ingrowth mesh;

wherein the ingrowth mesh is dimensioned such that if the implant is implanted immediately above the muscle layer in the abdominal wall of the patient or a member of the class of patients respectively, the epidermis would meet the ingrowth mesh and be able to attach therethrough directly to serosal tissue of a bowel segment inside the implant.

21. The implant according to claim 1, wherein the cylindrical part further comprises a healing device that prevents the implant from being distracted below the abdominal wall of the subject, the healing device also serving for sealingly closing the end of the implant.

22. The implant according to claim 21, wherein the healing device further includes cap means that surrounds and sealingly closes the end of the implant, the cap means comprising mating means for removable attachment to the mating means of the implant.

23. The implant according to claim 22, wherein cap means of the healing device further includes an O-ring serving for sealing against the exterior circumferential wall of the implant, and the implant includes a healing plate resting on the skin surface of the subject, wherein the healing plate has an external screw thread for coupling with a complementary internal screw thread on the cap means.

24. The implant according to claim 16, further comprising a healing device engaged with the implant to prevent the implant from being distracted below the abdominal wall of the subject, the healing device also serving for sealingly closing the protruding part and free end of the implant body.

25. The implant according to claim 24, wherein the healing device further includes cap means that surrounds and sealingly closes the end of the implant, the cap means comprising mating means for removable attachment to the mating means of the implant.

26. The implant according to claim 25, wherein cap means of the healing device further includes an O-ring serving for sealing against the exterior circumferential wall of the implant, and the implant includes a healing plate resting on the skin surface of the subject, wherein the healing plate has an external screw thread for coupling with a complementary internal screw thread on the cap means.

27. The method according to claim 18, which further comprises providing a healing device to the implant during a healing phase in order to protect the implant and prevent it from being retracted below skin level.

28. The method according to claim 27, which further comprises mounting a lid upon the healing device of the implant.

* * * * *